United States Patent [19]
Schaer

[11] Patent Number: 5,885,220
[45] Date of Patent: Mar. 23, 1999

[54] SPHYGMOMANOMETER CUFF

[75] Inventor: Andreas Schaer, Hindelbank, Switzerland

[73] Assignee: Disetronic Licensing AG, Burgdorf, Switzerland

[21] Appl. No.: 849,321

[22] PCT Filed: Nov. 21, 1995

[86] PCT No.: PCT/CH95/00274

§ 371 Date: Feb. 25, 1998

§ 102(e) Date: Feb. 25, 1998

[87] PCT Pub. No.: WO97/18750

PCT Pub. Date: May 29, 1997

[51] Int. Cl.[6] .................................................. A61B 5/02
[52] U.S. Cl. .................................................. 600/490
[58] Field of Search .................................. 600/490, 491, 600/492, 493, 494, 495, 496, 497, 498, 499; 606/202, 204; 128/DIG. 20, DIG. 15, 900

[56] References Cited

U.S. PATENT DOCUMENTS 3,757,772   9/1973   Goldblat et al. ........................ 600/499

*Primary Examiner*—George Manuel
*Attorney, Agent, or Firm*—Dorsey & Whitney

[57] ABSTRACT

The cuff for a sphygmomanometer comprises a flexible cover having an approximately rectangular area when unrolled and comprising a first short side and a second short side. The cover contains an air chamber in its interior which is connectable to a monitoring device. It has fixing means on its surface for fixing the cuff around a body limb. A flap, both sides of which are coated with attaching means for temporary attachment to the holding means, is attached to the second short side of the cover which flap folds both to the one surface and the other surface of the cuff and is attachable thereto by its attaching means.

17 Claims, 2 Drawing Sheets

SPHYGMOMANOMETER CUFF

BACKGROUND OF THE INVENTION

The present invention relates to a cuff for a sphygmomanometer comprising a flexible cover having an approximately rectangular area when unrolled and comprising a first short side and a second short side, said cover containing an air chamber in its interior comprising a connection to a monitoring device, and having fixing means on both its surfaces for fixing the cuff around a body limb, in which in the zone adjacent to the second short side of the cover attaching means are provided on both surfaces for temporary attachment to the fixing means.

Cuffs for sphygmomanometers have been known for a long time. They are comprised of a flexible cover, an air chamber connectable by a tube to a monitoring device, and a fixing means. The flexible cover is formed by a soft, usually washable material, contains an air chamber and is the carrier of a fixing means. The air chamber is either located in the flexible cover in the form of a bag or is formed by the flexible cover itself. The fixing means has the purpose of bringing and holding the cuff in the right position when it is wrapped around the arm, the leg or another limb. The fixing means itself is designed in different forms depending on the type of cuff.

In case of cuffs which are put on by the patient himself, a loop, for example in the form of a bow, through which the other end of the cuff is pulled is arranged at one end of the flexible cover. The overlapping part of the cuff is attached to that side of the flexible cover facing away from the patient. Shell-type cuffs are also known where one part of the flexible cover consists of a flexible half-shell; said flexible halfshell permits a loose fixation to the limb concerned, a Velcro-type fastener being additionally necessary for final attachment.

Cuffs put on by another person usually consist of a flexible cover only which may be wrapped around the body limb concerned and fixed around said limb by means of a Velcro-type fastener or another fixation means.

All these known cuffs have in common that the flexible cover consists of an inner side facing the patient and an outer side facing away from the patient. Changing the sides is not possible. The inner part of the flexible cuff may only be attached to the outer part thereof. Therefore, they are suitable either for a left body limb only or a right body limb only, because the tube connecting the air chamber and the monitoring device or the air chamber itself cannot be positioned ideally for both body limbs. In addition, the patient must always pull the overlapping part through the loop in the same direction and fix it to the outer side of the flexible cover in a simpler embodiment.

Blood pressure should always be measured on that limb where the higher values are registered. This is different for every person. In addition, the measurement in patients whose blood pressure is taken several times during 24 hours, must always be carried out on that limb which is under the least stress in the normal course of a day (referred to as the "non-dominant" limb in the technical language). Said non-dominant limb also differs individually.

A cuff which may be wrapped both around a left body limb and a right body limb is known from EP-A-0 251 273. The disadvantage of this known cuff is that it requires two non-changeable sides, one facing towards and the other facing away from the body. Since the same side is always facing the body, the inflatable bag must be turned when moving the cuff from the left to the right limb so as to put the tube on the sphygmomanometer into an ideal position.

Another cuff which may be wrapped both around a left and a right body limb is known from EP-A-0 274 735. This is a cuff for ambulant haemodynamometry which is applied by the patient himself. In this embodiment, the overlapping part is pulled through the loop from different directions, depending on whether a left or right body limb is measured. The inflatable bag which is positioned exchangeably in the interior of the flexible cover must be turned to ensure that the tube to the sphygmomanometer runs in an ideal manner.

SUMMARY OF THE INVENTION

It is the purpose of the present invention to overcome these disadvantages. The invention is based on the objective to provide a cuff which requires the fewest possible manipulations to be adapted for use on a left or right body limb without the selection of the body limb to which the cuff is attached influencing the ideal positioning of the air chamber or the tube, at the same time permitting attachment of the cuff from various directions depending on the body limb.

The present invention solves said objectives with a cuff in which in the zone adjacent to the second short side of the cover attaching means are provided on both surfaces for temporary attachment to the fixing means. The advantages provided by the invention are substantially those that the cuff according to the invention may be adapted for use both on a left and a right body limb by very few manipulations.

The figures illustrate several embodiments of the invention.

DESCRIPTION OF THE PREFERRED EMBODIMENTS

Figure 1:
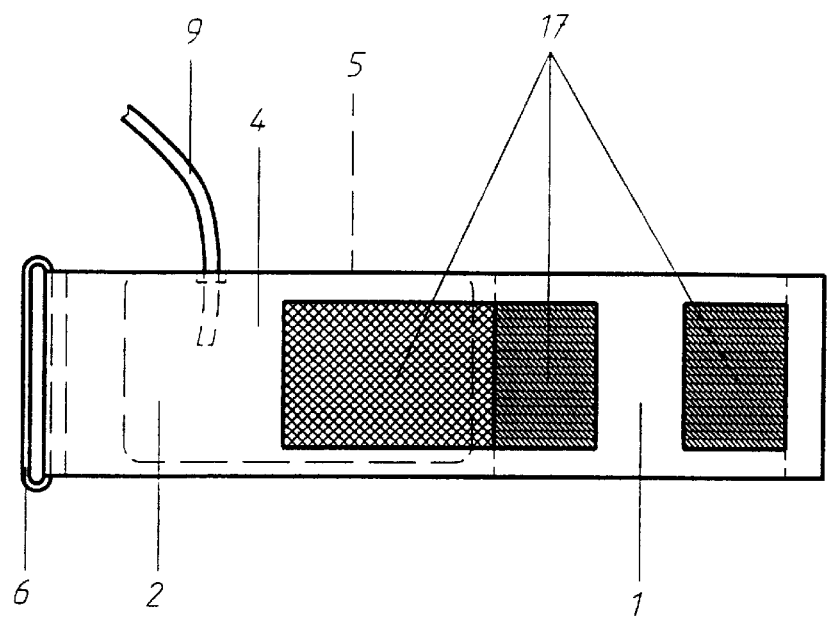
FIG. 1 is a top view on a cuff according to the prior art.

As shown in FIG. 1, the cuff according to the prior art consists of a flexible cover 1, an air chamber 2, a tube 9 to a monitoring device, said flexible cover 1 comprising an inner side 4 facing towards the patient and an outer side 5 facing away from the patient and a fixing means 6, 17 which consists of a metallic fixing loop 6 and a Velcro-type or hook fastener 17 attached to the flexible cover 1. Such a Velcro-type fastener consists of a Velcro-tape and a fluffy part. The adjustment of the length and thus the positioning of the cuff to the member concerned is carried out with or without the loop 6 in connection with the Velcro-type or hook fastener 17.

Figure 2:
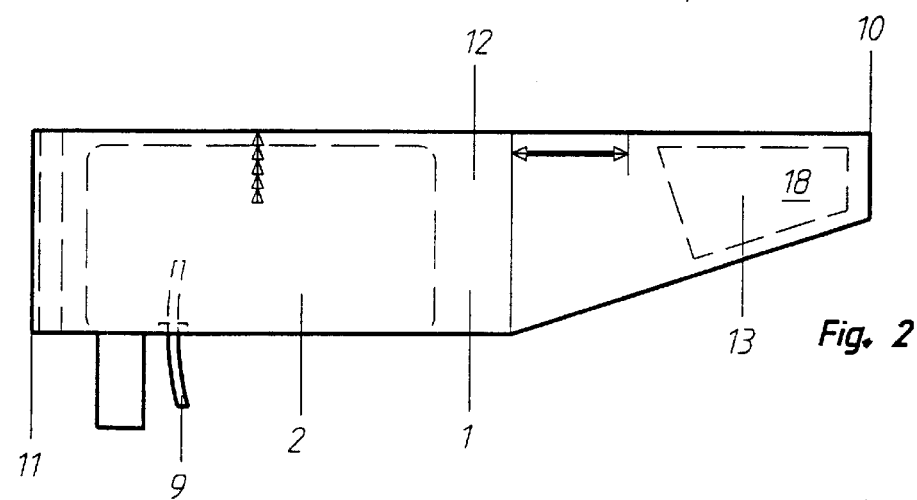
FIG. 2 is a top view on a cuff according to the invention.

The cuff for a sphygmomanometer shown in FIG. 2 comprises a flexible cover 1 having an approximately rectangular area when unrolled and comprising a first short side 11 and a second short side 10. The cover 1 contains an air chamber 2 in its interior which has a connection 9 to a monitoring device and has fixing means 12 on both its surfaces 4, 5 for fixing the cuff around a body limb.

In the trapeze-shaped zone 18 adjacent to the second short side 10 of the cover 1, attaching means 13 are provided on both surfaces 4, 5 for temporary attachment to the holding means 12. Since the attaching means 13 in the zone 18 are present on both surfaces 4, 5 (i.e. on and behind the illustrated plane in FIG. 2), attaching means are preferably chosen which cannot cooperate with the clothes usually worn by the patient (fluffy parts). Possible attaching means are therefore primarily cooperating burls, grooves, magnetic parts, adhesive strips and similar elements.

In case of the embodiment shown in FIG. 2 (without loop as in FIG. 1), the flexible cover 1 is wrapped around the desired body limb and then attached to the holding means 12 of the cover 1 by the attaching means 13 present in zone 18.

If a loop 6 is provided on the first short side 11 as in the embodiment of the prior art according to FIG. 1, the flexible cover 1 is pulled through said loop 6 until the inner side (surface 4 in FIG. 4) of the cover 1 encircles the body limb. The part of the flexible cover 1 pulled through the loop is folded over in the opposite direction and attached on the outer side (surface 5 in FIG. 4) of the flexible cover 1 by the attaching means 13 in zone 18.

Figure 3:
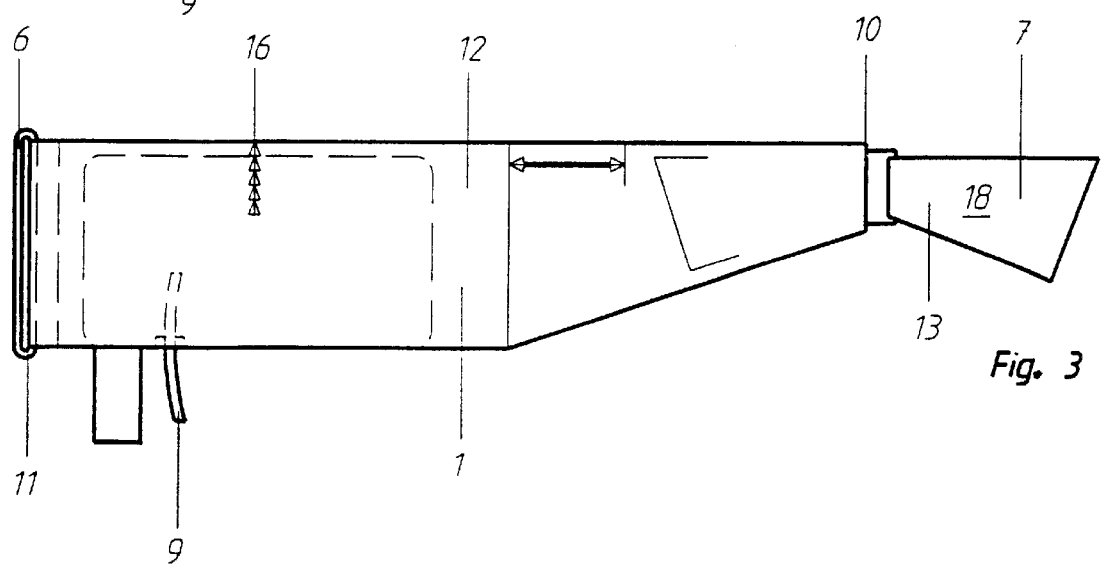
FIG. 3 is a top view of a preferred embodiment of a cuff according to the invention.
Figure 4:
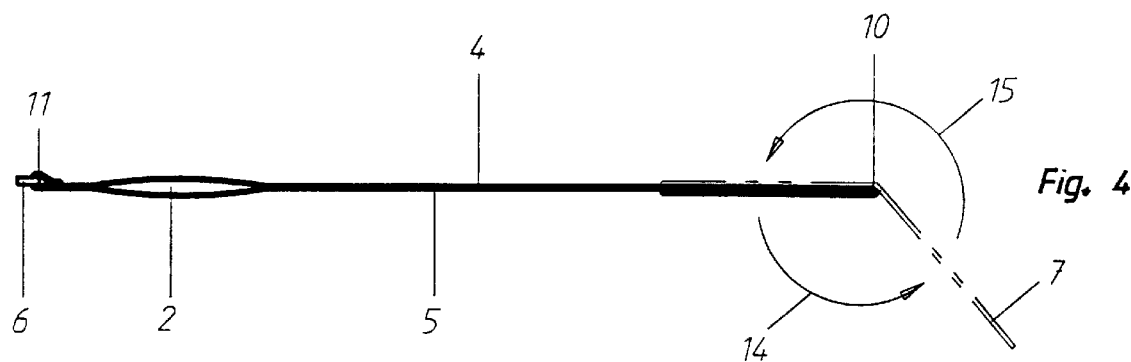
FIG. 4 is a side view of the cuff according to FIG. 3.

A preferred embodiment of the invention illustrated in FIGS. 3 and 4 differs insofar from the embodiment shown in FIG. 2 as a metallic loop 6 is present on the first short side 11 and that a four-cornered flap 7 attachable on the inner or outer side of the flexible cover 1 is present as zone 18 on the second short side 10. The flap 7 is equipped on both sides with attaching means 13 in the form of a Velcro-type fastener. Due to the fact that the flap 7 is equipped on both sides with attaching means 13 in the form of Velcro-type fasteners or other structures acting analogously said flap may be attached both to the inner side facing the patient (surface 4) and the outer side facing away from the patient (surface 5) of the flexible cover 1. The latter distinction, therefore, becomes basically no longer necessary.

Figure 5:
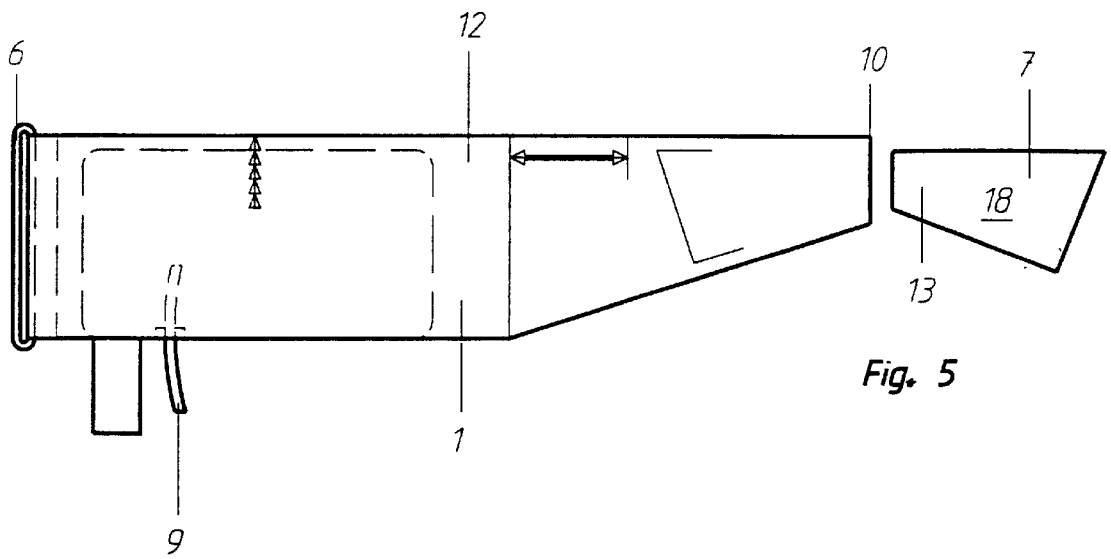
FIG. 5 is a top view of another embodiment of the cuff according to the invention in a dismembered state.
Figure 6:
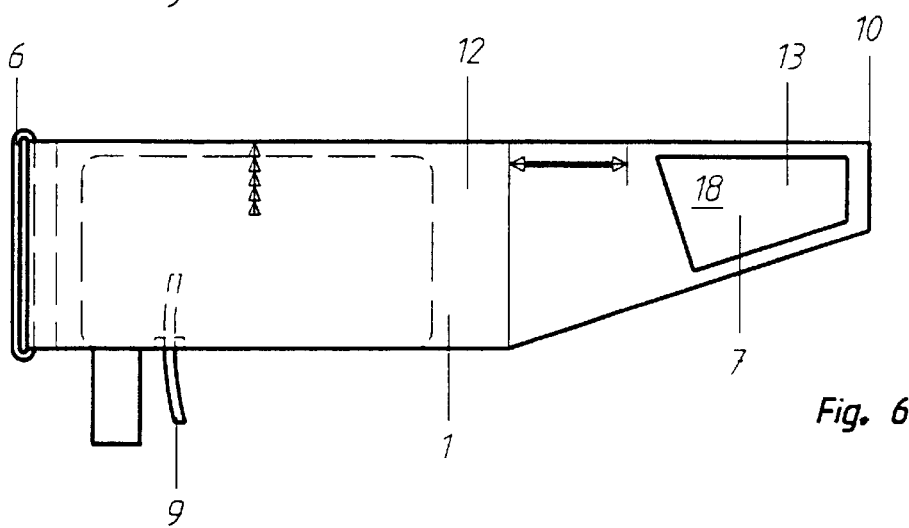
FIG. 6 is a top view of the cuff according to FIG. 5 in an assembled state.

In another embodiment of the invention shown in FIGS. 5 and 6, zone 18 is a flap 7 which is separated from the cover 1. Said separate flap 7 may either be attached to the one or to the other surface of the cover 1 (on or below the illustrated plane in FIG. 5) by its attaching means 13. In FIG. 6, the flap in trapeze form is attached to the upper side of the cover 1 adjacent to the second short side 10 so that the cuff may be used in the same way as in the embodiments according to FIGS. 3 and 4.

In the following, the use and mode of operation of the cuff according to the invention as shown in FIGS. 3 and 4 will be described in detail.

In order to position the cuff on the body limb concerned, the flap 7 is first to attached to one of the two surfaces 4, 5 of the flexible cover 1. This attachment must take place near the second short side 10 of the flexible cover 1. The flap 7 consists of two sides both of which are provided with attaching means 13. The attaching means 13 cooperate with the holding means 12 provided on the two surfaces 4, 5 of the cover 1. Possible combinations for the holding means 12/attaching means 13 in this embodiment are Velcro-type fasteners, adhesive fasteners, magnetic fasteners and such like.

In a preferred embodiment the flap 7 itself is provided with a Velcro-type tape and the flexible cover 1 is completely covered with a fluffy material which cooperates with the Velcro-type tape. If the flap 7 is attached on the flexible cover 1, it still has a free side equipped with a Velcro-type tape. As shown below, this side has the purpose of positioning the flexible cover 1 correctly. Once the flap 7 has been attached to the flexible cover 1, the cuff according to the invention may be positioned like known cuffs.

In the preferred embodiment shown in FIGS. 3 and 4, a metallic loop 6 is present on the short side 11 of the flexible cover 1 opposite the flap 7. In this embodiment that surface 4, 5 of the cover 1, which the flap 7 was attached to, inevitably becomes the outer side of the flexible cover 1. In FIG. 4, for example, this is the one surface 5. The flexible cover 1 is pulled through the loop 6 until the inner side (surface 4 in FIG. 4) of the cover 1 encircles the body member. Various markings 16 on the outer side of the flexible cover 1 permit the user to position the cuff in such a way that the centre of the air chamber 2 is positioned directly over the artery to be measured (e.g. the *Arteria brachialis*). If the air chamber 2 is positioned correctly, that part of the flexible cover 1 which was pulled through the loop 6 and which supports the flap 7 is folded over in the opposite direction and attached to the outer side of the flexible cover 1 by means of that side of the flap which is still free.

In the preferred embodiment according to FIGS. 3 and 4, the flexible cover 1 is fully covered with a fluffy material so that the flap 7 which is covered by a Velcrotype tape may be attached to any location of the flexible cover 1. It is also conceivable that the flap 7 may only be attached to certain locations of the flexible cover 1 as is the case with known cuffs. It is an advantage if the flap 7 can be attached to any location, because otherwise different materials are required and the arrangement of said other materials must be calculated accurately which results in higher production costs.

If it is now intended to fasten the cuff around an opposite limb (e.g. the right upper arm instead of the left upper arm), the flap 7 and the part supporting it must first be separated from the outer side of the cover 1 and then pulled through the loop 6. Then the flap 7 is folded from the one surface (5 in FIG. 4) in the direction of the arrows 14, 15 to the other surface (4 in FIG. 4) of the flexible cover 1 so that the original inner side becomes the outer side. The further procedure concurs with that described above.

It is also possible to use cuffs without loops 6. Depending on the body limb, the flap 7 of these cuffs is also attached to the one or the other surface 4, 5 of the flexible cover 1. If such a loop 6 is missing, however, the flap is fastened to the relevant inner side of the flexible cover 1, because folding it in the opposite direction is not applicable.

I claim:

1. A cuff for a sphygmomanometer comprising a flexible cover having an approximately rectangular area when unrolled and having a first short side, a second short side, and top and bottom surfaces, the cover containing an air chamber having a connection to a monitoring device, the cover having fixing means on the top and bottom surfaces, one of the top and bottom surfaces of the flexible cover contacting a body limb when the cuff is affixed around the body limb, and a zone adjacent the second short side of the cover having attaching means on a first and second surface for temporary attachment to the fixing means.

2. A cuff according to claim 1, wherein the zone is a flap attached to the second short side of the cover, the flap being foldable either to the top surface or the bottom surface of the cover and attachable thereto by the attaching means.

3. A cuff according to claim 1, wherein the zone is a separate flap from the cover, wherein the flap is attachable either to the top surface or the bottom surface of the cover by the attaching means.

4. A cuff according to claim 1, wherein the fixing means are hooks and the attaching means are loops which, together, act as a Velcro-type fastener.

5. A cuff according to claim 1, wherein the fixing means are loops and the attaching means are hooks which, together, act as a Velcro-type fastener.

6. A cuff according to claim 1, wherein the fixing means and the attaching means are magnetic elements.

7. A cuff according to claim 1, wherein the fixing means and the attaching means are a cooperative adhesive fastener.

8. A cuff according to claim 1, wherein on the first short side of the cover a retaining loop for introducing the second short side is provided.

9. A cuff according to claim 1, wherein the zone is shaped in trapeze form.

10. A cuff according to claim 1, wherein the fixing means and the attaching means cooperate with regard to their area.

11. A cuff for a sphygmomanometer comprising:

(a) a flexible cover having a first short side, a second short side, and top and bottom surfaces, the flexible cover containing an air chamber having a connection to a monitoring device, and wherein the flexible cover includes a fixer on the top and bottom surfaces; and (b) an attacher adjacent the second short side, the attacher having a first surface and a second surface, wherein the attacher has attaching means on both the first surface and the second surface for selective operable connecting to the fixer.

12. The cuff of claim 11 wherein the attacher is a flap operably connected to the second short side of the flexible cover such that it can fold to attach to the cover on one of the top and bottom surfaces of the cover.

13. The cuff of claim 11 wherein the attacher is a flap which may be attached to one of the top and bottom surfaces of the flexible cover on either the first or second surface.

14. A cuff for a sphygmomanometer comprising:

(a) a flexible cover having a first short side, a second short side, and top and bottom surfaces, the flexible cover containing an air chamber having a connector for connection to a monitoring device and including a holding region on the top and bottom surfaces, one of the top and bottom surfaces of the flexible cover contacting a body limb when the cuff is around the body limb; and (b) a flap operably associated with one of the short sides of the flexible cover, the flap having a first surface and a second surface, wherein the flap has attaching means on both the first surface and the second surface for selective temporary operable connecting to the holding region.

15. The cuff of claim 14 wherein the flap is connected to one of the short sides and further comprising a loop attached to the other of the short sides of the flexible cover, wherein the flap can fold through the loop and allow the attaching means to attach to the holding region.

16. The cuff of claim 14 wherein the flap is separate from the flexible cover and selectively attachable to the holding region of one of the top and bottom surfaces of the flexible cover.

17. The cuff of claim 16, wherein at least one of the top and bottom surfaces carry means for positioning the cuff so that the air chamber is selectively positionable with respect to a limb.

* * * * *